United States Patent [19]

Nerome et al.

[11] Patent Number: 4,826,687
[45] Date of Patent: May 2, 1989

[54] INFLUENZA VACCINE

[75] Inventors: Kuniaki Nerome; Akira Oya, both of Tokyo; Kunio Ohkuma, Kumamoto; Atsuo Inoue, Funabashi, all of Japan

[73] Assignees: National Institute of Health; Daiichi Seiyaku Co., Ltd., both of Tokyo; Juridical Foundation the Chemo-Sero-Therapeutic Research Institute, Kumamoto, all of Japan

[21] Appl. No.: 867,539

[22] Filed: May 28, 1986

[30] Foreign Application Priority Data

Jun. 6, 1985 [JP] Japan ................. 60-123341

[51] Int. Cl.$^4$ .............. A61K 39/22; A61K 39/12; B01J 13/02
[52] U.S. Cl. .................... 424/450; 264/4.6; 424/89; 428/402.2; 436/829; 514/885
[58] Field of Search ............ 264/4.6; 428/402.2; 424/89, 450; 514/885; 436/829

[56] References Cited

U.S. PATENT DOCUMENTS

| 4,009,258 | 2/1977 | Kilbourne | 424/89 |
|---|---|---|---|
| 4,117,113 | 9/1978 | Allison et al. | 424/89 |
| 4,196,191 | 4/1980 | Almeida et al. | 424/89 |
| 4,261,975 | 4/1981 | Fullerton et al. | 424/89 |
| 4,438,052 | 3/1984 | Weder et al. | 264/4.6 |
| 4,565,696 | 1/1986 | Heath et al. | 424/450 |
| 4,663,161 | 5/1987 | Mannino et al. | 424/89 |
| 4,663,311 | 5/1987 | Tenu et al. | 514/26 |

FOREIGN PATENT DOCUMENTS 2146525 4/1985 United Kingdom ............ 424/450

OTHER PUBLICATIONS

Oxford et al., "The Interaction of Influenza Virus Hæmagglutinin with Phospholipid Vesicles-Morphological and Immunological Studies", J. Gen. Virol., vol. 52, pp. 329-343, 1981.

Almeida et al., "Formation of Virosomes from Influenza Subunits and Lipsomes", The Lancet, pp. 899-901, Nov. 8, 1975.

Primary Examiner—Richard D. Lovering
Attorney, Agent, or Firm—Fleit, Jacobson, Cohn & Price

[57] ABSTRACT

This invention relates to a novel influenza vaccine comprising a complex of HANA antigen and an MDP derivative.

The novel vaccine is prepared by mixing an influenza HANA antigen and at least one MDP derivative in a suitable medium; solubilizing the resulting mixture with a surface active agent capable of being removed by dialysis, the solubilization being conducted in the presence or absence of cholesterol, lecithin and dicetyl phosphate or a mixture thereof; and then removing the surface active agent therefrom by dialysis to obtain an influenza vaccine comprising artificial vesicle-like particles of a complex of HANA antigen and MDP derivative, where the MDP derivative forms a membrane of the particle (corresponding to the lipid membrane of natural influenza virus particle) on the surface of which there exists the HANA antigen being bonded to the MDP derivative so as to form the complex. Thus, said artificial vesicle-like particle of the HANA antigen-MDP derivative complex has nearly the same particle size and shape as the natural influenza virus particle.

The novel vaccine has an improved immunogenicity compared with the conventional vaccine.

7 Claims, 4 Drawing Sheets (×150,000)

(×150,000)

(×200,000)

INFLUENZA VACCINE

BACKGROUND OF THE INVENTION (1) Field of the Invention

This invention relates to a novel influenza vaccine, in particular to an influenza vaccine consisting of artificial vesicle-like particles of a complex of HANA antigen derived from influenza virus, known as the active component of the vaccine, and a muramyldipeptide derivative (hereunder referred to as MDP derivatives) known as synthetic adjuvant, the artificial particles being similar in size and shape to naturally occurring influenza virus particles. This invention also relates to a process for preparing such a novel vaccine.

(2) Description of the Prior Art

Since the vaccination effect of presently used influenza HA vaccines is subject to fluctuation by mutations which occur on HA (hemagglutinin) molecule of the prevailing virus, it is strongly desired to develop more effective vaccines than the conventional ones.

One of the recent approaches in influenza vaccine development is directed to a component vaccine consisting of HA and NA (neuraminidase) as the main ingredients, i.e., influenza HANA vaccine. The resulting vaccine comprised of purified HA and NA is considered an ideal vaccine in terms of safety and effect and has already been put to practical use in England. Actually, however, the effect of the vaccine is still insufficient.

On the other hand, another approach is directed to utilization of adjuvants. This work has resulted in the development of muramyldipeptide (MDP) as well as many kinds of MDP derivatives which improved on the immunopotentiation and the like of MDP by appropriate chemical modification, as novel adjuvant materials. Regarding these MDP derivatives, it is, for example, reported by Kotani et. al., in YAKUGAKU ZASSHI 103(1), 1–27, 1983 that 6-0-(2-tetradecylhexadecanoyl) MDP was administered to guinea pigs together with influenza vaccine (i.e., HANA vaccine) containing highly purified HA and NA as main ingredients, and that effective adjuvant effect was obtained. However, HANA vaccine obtained by simply adding these MDP derivatives into a vaccine as an adjuvant does not provide the vaccine with adequate effect.

SUMMARY OF THE INVENTION

Accordingly, the primary object of the present invention is to provide a novel influenza vaccine having an improved immunogenicity compared with the conventional vaccine.

Another object of the present invention is to provide a novel influenza vaccine comprising artificial vesicle-like particles of HANA antigen-MDP derivative complex having nearly the same particle size and shape as the natural virus particles.

These and other objects of the present invention will be clear from the following description.

According to the present invention, there is provided an influenza vaccine comprising artificial vesicle-like particles of a complex of HANA antigen and at least one MDP derivative, where the MDP derivative forms a membrane of the particle (corresponding to the lipid membrane of natural influenza virus particle) on the surface of which there exists the HANA antigen being bonded to the MDP derivative so as to form the complex, which thus differs from the vaccine obtained by simply mixing a vaccine and an adjuvant. Thus, the artificial vesicle-like particles of a complex of HANA antigen and MDP derivative obtained according to the present invention have nearly the same particle size and the same shape as the natural virus particles.

DESCRIPTION OF THE PREFERRED EMBODIMENTS

The novel influenza vaccine can be prepared by the following special process.

Figure 1:
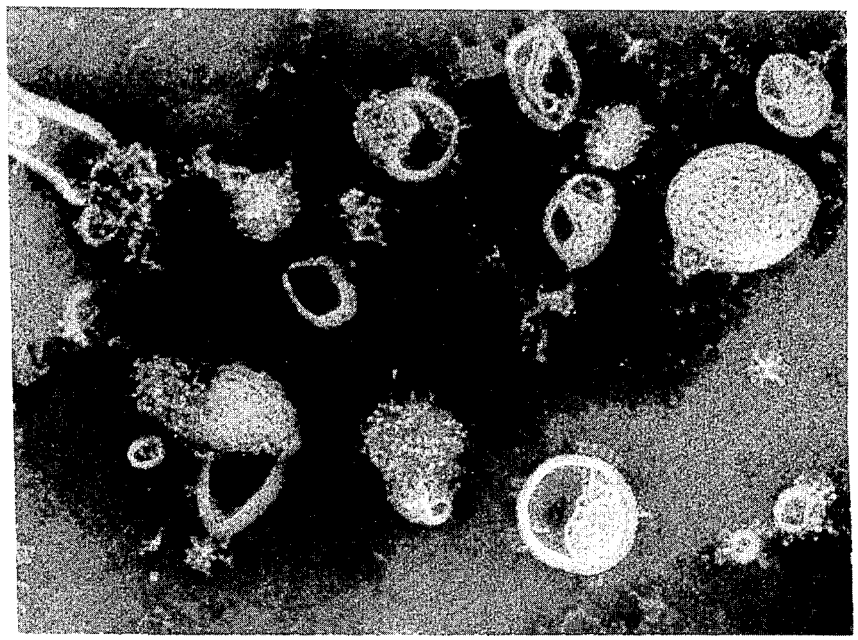
FIGS. 1 and 2 are electron photomicrographs ($\times 150,000$) of sample vaccine No. 1 and sample vaccine No. 2 of the present invention, respectively.
Figure 2:
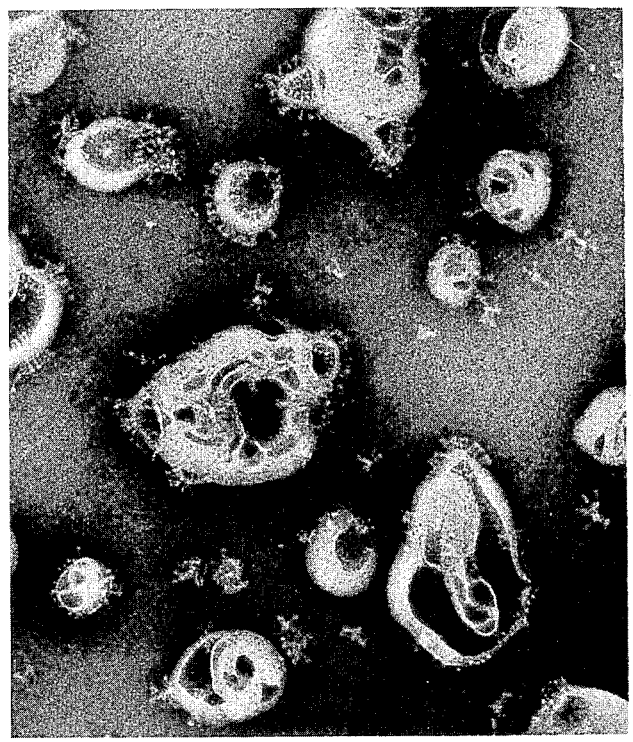
Figure 3:
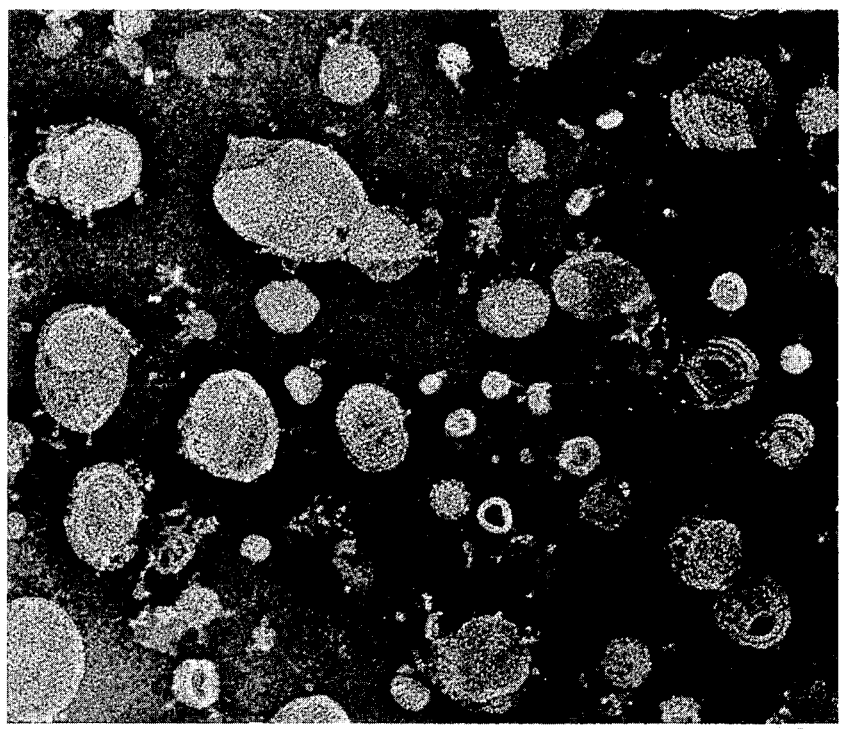
FIG. 3 is an electron photomicrograph ($\times 200,000$) of sample vaccine No. 4 of the present invention.

An influenza HANA antigen and an MDP derivative are firstly mixed in a weight ratio between 10/1 and 1/300 in a suitable buffer solution, for example, phosphate-buffered saline, and then the resulting mixture is solubilized by adding an effective amount (0.1–10 w/V %) of surface active agent thereto. Thereafter, the surface active agent is removed therefrom by dialysis to obtain a novel HANA antigen—MDP derivative complex. In this connection, it is important to use a surface active agent which can be removed by dialysis. Examples of such surfactants include octylglucoside, sodium cholate and the like. Referring to FIGS. 1 to 3, the HANA antigen—MDP derivative complex thus obtained forms a so-called virosome in which the MDP derivative per se enables formation of artificial vesicle-like particles and HANA antigens are combined on the surface thereof through their narrow ends so that they have the same orientation as on the natural virus particles.

According to another aspect of the present invention, there can be used MDP derivatives together with (i) cholesterol (ii) lecithin and dicetyl phosphate or (iii) a mixture of (i) and (ii), etc., which promote the ability of MDP derivative artificial vesicle-like particles to form. In this case, it is preferable to employ the following weight ratio:

For using cholesterol: an MDP derivative/cholesterol = 1/0 to 1/5, more preferably 1/0.5 to 1/2

For using lecithin: an MDP derivative/lecithin = 1/0 to 1/50, more preferably 1/1 to 1/20

For using dicetyl phosphate: Lecithin/dicetyl phosphate = 1/0.05 to 1/2, more preferably 1/0.5 to 1/1

In addition, in accordance with this aspect of the invention, it is not necessarily required to use the surface active agent and to conduct dialysis, so that this aspect has an advantage in that MDP derivative vesicle-like particles can be formed by, i.e., conventional sonication (the ultrasonic method), microinjection, reverse phase evaporation or the like.

MDP derivatives usable in the present invention include many kinds of appropriate chemical modifications of MDP. Such MDP derivatives are described, i.e., in Japanese Patent Public Disclosure (KOKAI) Nos. 52-46020, 52-156812, 54-73729, 54-130517, 55-19236, 55-28932, 55-28933, 56-18996, 56-49396 and 60-78997.

It is preferable to use an MDP higher fatty ester having the following formula:

$$\begin{array}{c} CH_2O\text{—}Q \\ \diagup\text{—}O \\ HO\diagup\diagdown\diagup\diagdown H.OH \\ | \\ NHCOCH_3 \\ CH_3CHCO\text{—}A\text{—}D\text{-isoGln} \end{array}$$

wherein Q represents a synthetic higher fatty acid residue having 20 to 60 of total carbon atoms;
A represents L-alanine, L-serine or glycine; and
iso Gln represents isoglutamine.

It is more preferable to use 6-0-(2-tetradecyl hexadecanoyl) MDP referred as B30-MDP. These fatty esters are described in Japanese Patent Public Disclosure (KOKAI) No. 4-130517.

It is also preferable to use the MDP derivative having the following formula:

$$\begin{array}{c} CH_2OH \\ \diagup\text{—}O \\ HO\diagup\diagdown\diagup\diagdown H.OH \\ | \\ NH\text{—}Acyl \\ \phantom{xxxx} CONH_2 \\ \phantom{xxxx} | \\ CH_3CHCO\text{—}X\text{—}\underbrace{NHCHCH_2\text{—}CH_2CO}_{D}\text{—}Y \end{array}$$

wherein X represents an amino acid such as L-alanine, L-serine, L-valine and glycine;
Y represents $$-NH-A \text{ or } -NHCH(CH_2)_n-NHCO-A$$
$$\phantom{-NH-A \text{ or } -NH}|$$
$$\phantom{-NH-A \text{ or } -NH}R_1$$

wherein $R_1$ is hydrogen atom, lower alkyl group, carboxamido group or carboxyl group; n is 1 to 6; and A is a saturated or unsaturated aliphatic hydrocarbon residue having 8 to 30 of carbon atoms with or without branches. More preferable example of such derivatives includes $N^\alpha$-(N-acetyl muramyl-L-alanyl-D-isoglutaminyl)-$N^\epsilon$-stearoyl-L-lysine, referred as MDP-Lys (L18).

Furthermore, it is preferable to use $N^\alpha$-(N-acetyl muramyl-N-methyl-L-alanyl-D-isoglutaminyl)-$N^\epsilon$-stearoyl-L-lysine, referred as MDP (MeAla)-Lys (18), which is described in Japanese Patent Public Disclosure No. 60-78997.

The HANA antigen used in the present invention can be obtained by the steps of purifying influenza virus by high-speed centrifugal separation or chemical treatment of allantoic fluid harvested from influenza virus infected eggs, solubilizing the purified virus with a nonionic surface active agent such as Triton x -100 and NP-40 or an anionic surface active agent such as sodium deoxycholate and sodium cholate, or a cationic surface active agent such as cetyl trimethyl ammonium, or decomposing the purified virus with an organic solvent such as ether, and then further purifying the resultant by sucrose density-gradient centrifugation, affinity chromatography or the like.

The present invention will be illustrated more concretely by referring to the following non-limitative examples.

EXAMPLE 1

Preparation of influenza HANA antigen

Influenza A/Bangkok/1/79 ($H_3N_2$) virus was grown in embryonated hen's eggs and purified by subjecting the grown virus to high-speed centrifugal separation (23,000 r.p.m., 90 minutes), low-speed centrifugal separation (6,000 r.p.m., 60 minutes) and sucrose density-gradient centrifugation (30,000 r.p.m., 3 hours). There was then added Triton x-100 to the resulting virus solution in such amount that the final concentration of the Triton x-100 became 1%, the virus was solubilized by fully agitating it, after which purified HANA antigen solution was obtained by sucrose density-gradient centrifugation.

Preparation of vaccine and immune test

Using the purified HANA antigen solution obtained above, four kinds of vaccine samples, the compositions of which are shown in Table 1, were prepared as follows.

The respective ingredients were mixed and then octyl glucoside was added in such amount that the final concentration of the glucoside became 3 wt %. After the ingredients were solubilized, dialysis into a phosphate-buffered saline was conducted according to the conventional method. The HANA antigen concentration of each sample thus obtained was adjusted to 0.8 μg N/ml and then inoculated at a dose of 0.5 ml/mouse into the peritoneum of each of a group of 15 DDY mice (4 weeks old, ♀). Thereafter, the mice were divided into three groups of five each and blood was collected from the mice of the respective groups at one week, 2 weeks and 3 weeks, and Hemagglutinin Inhibitation Test was conducted according to the WHO method to measure antibody-forming ability.

DDY mice were also immunized with the aforesaid respective samples according to the same method as described above, and infected with virus of the strain used for preparing the vaccine 2 weeks later. The lungs of the mice were removed 4 days later. Plaque forming test by MDCK cell was conducted on the lungs to measure the amount of virus in the lung. The results obtained are shown in Table 1.

TABLE 1

| Sample No. | Composition | | Antibody-forming ability (HI value) | | | Infection protective test result | |
|---|---|---|---|---|---|---|---|
| | | | 1 week | 2 weeks | 3 weeks | Existence of pneumonia | Amount of virus (number/ml) |
| 1 | HANA | 0.8 μgN | <16 | 64 | 128 | no | 10> |
| | B30-MDP | 50 μg | | | | | |
| 2 | HANA | 0.8 μgN | 64 | 128 | 256 | no | 10> |
| | B30-MDP | 50 μg | | | | | |

TABLE 1-continued

| Sample No. | Composition | | Antibody-forming ability (HI value) | | | Infection protective test result | |
|---|---|---|---|---|---|---|---|
| | | | 1 week | 2 weeks | 3 weeks | Existence of pneumonia | Amount of virus (number/ml) |
| 3 | Cholesterol | 50 μg | | | | | |
| | HANA | 0.8 μgN | <16 | 32 | 64 | no | 10> |
| | B30-MDP | 50 μg | | | | | |
| | Lecithin | 250 μg | | | | | |
| | Dicetyl phosphate | 250 μg | | | | | |
| 4 | HANA | 0.8 μgN | 32 | 64 | 512 | no | 10> |
| | MDP-LYS (L18) | 50 μg | | | | | |
| | Lecithin | 250 μg | | | | | |
| | Dicetyl phosphate | 250 μg | | | | | |
| 5 (Comparative example) | HANA | 0.8 μgN | <16 | 16 | 32 | Present | $2.9 \times 10^3$ |

As is obvious from the results shown in Table 1, all vaccines of the present invention have superior antibody-forming ability to comparative examples consisting of only HANA.

Observing the shapes of the vaccines of sample Nos. 1, 2 and 4 with an electron microscope, it was ascertained that the MDP derivative artificial vesicle-like particles having the same size and the same shape as the natural influenza virus particles, on the surface of which the HANA antigens are bonded to the MDP derivative so as to form the complex were clearly formed as shown in FIGS. 1 to 3.

Figure 4:
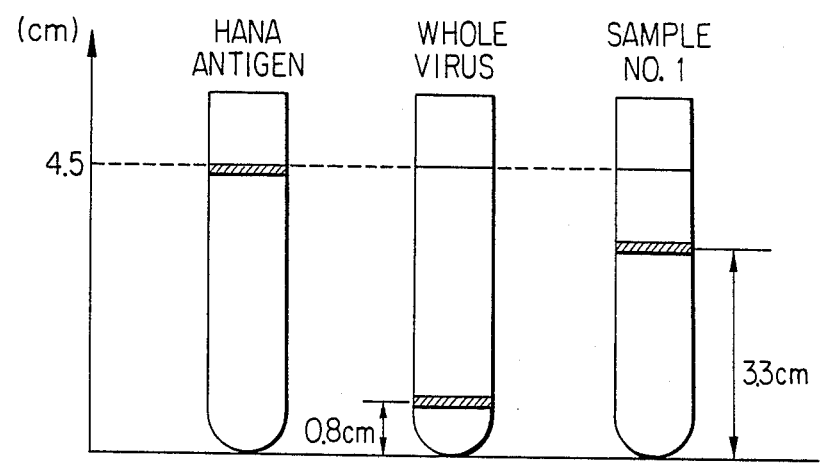
FIG. 4 represents a comparison of bands of density by the sucrose density-gradient centrifugation method to ascertain formation of the complex of the present invention.

In order to determine whether the above prepared sample No. 1 forms a complex, the densities of the HANA antigen, whole virus and sample No. 1 were measured by sucrose density-gradient centrifugation. As is obvious from the results shown in FIG. 4, sample No. 1 appeared as a band at a quite different position from the positions of HANA antigen and whole virus, so that sample No. 1 can be concluded to form a complex which differs from HANA antigen and whole virus.

EXAMPLE 2

HANA antigen was prepared by the same method as set forth in example 1 except for using influenza A/-Philippine/2/82 (H3N2) strain. The HANA antigen was mixed with the ingredients shown in Table 2, after which the mixture was subjected to a ultrasonic treatment for 8 minutes by Heat Systems W375 Sonicator equipped with a cup horn [range: 2.5] (Heat System-Ultrasonics., Inc.). The antibody-forming ability of each sample thus obtained was measured by the same method as set forth in example 1.

The results obtained are shown in table 2, which show that the vaccines of the present invention have good antibody-forming ability.

TABLE 2

| Sample No. | Composition | | HI value (elapsed 3 weeks) |
|---|---|---|---|
| 6 | HANA | 1.0 μgN | 512 |
| | B30-MDP | 30 μg | |
| 7 | HANA | 1.0 μgN | 512 |
| | B30-MDP | 30 μg | |
| | Lecithin | 450 μg | |
| | Dicetyl phosphate | 50 μg | |
| 8 | HANA | 1.0 μgN | 1024 |
| | B30-MDP | 30 μg | |
| | Cholesterol | 50 μg | |
| 9 | HANA | 1.0 μgN | 1024 |
| | MDP-LYS (L18) | 30 μg | |
| | Lecithin | 450 μg | |
| | Dicetyl phosphate | 50 μg | |
| 10 | HANA | 1.0 μgN | 512 |
| | MDP-LYS (L18) | 30 μg | |
| | Cholesterol | 50 μg | |
| Comparative example 11 | HANA | 1.0 μgN | 256 |

As is obvious from the above examples 1 and 2, the influenza vaccine of the present invention has good immunogenicity and improved influenza infection protective properties.

What is claimed is:

1. Influenza vaccine comprising complex of HANA antigen and at least one MDP derivative, wherein the MDP derivative forms artificial vesicle-like particles and has the formula:

$$\begin{array}{c} CH_2O-Q \\ \diagup -O \\ HO \diagup \diagdown O \diagdown H.OH \\ | \\ NHCOCH_3 \\ CH_3CHCO-A-D\text{-isoGln} \end{array}$$

wherein Q is a synthetic higher fatty acid residue having a total of 20 to 60 carbon atoms, A is a member selected from the group consisting of L-alanine, L-serine and glycine, and iso Gln is isoglutamine.

2. Influenza vaccine as set forth in claim 1, wherein the NDP derivative is 6-O-(2-tetradecyl hexadecanoyl) MDP.

3. Influenza vaccine as set forth in claim 1, wherein the weight ratio of influenza HANA antigen to the MDP derivative is between 10/1 and 1/300.

4. Influenza vaccine as set forth in claim 1, wherein the artifical vesicle-like particles of the MDP derivative contain cholesterol, or lecithin and dicetyl phosphate.

5. Influenza vaccine as set forth in claim 4, wherein chlolesterol is contained in an amount such that the weight ratio of MDP derivative to cholesterol is 1/0 to 1/5.

6. Influenza vaccine as set forth in claim 4, wherein lecithin and dicetyl phosphate are contained in an amount such that the weight ratio of MDP derivative to lecithin is 1/0 to 1/50 and the weight ratio of lecithin to dicetyl phosphate is 1/0.05 to 1/2.

7. Influenza vaccine as set forth in claim 1, wherein the influenza HANA antigen is an antigen prepared by subjecting influenza virus to purification.

* * * * *